US005193287A

United States Patent [19]
Coulter et al.

[11] Patent Number: 5,193,287
[45] Date of Patent: Mar. 16, 1993

[54] APPARATUS FOR PERFORMING SCROTAL CIRCUMFERENCE MEASUREMENT ON BULLS

[75] Inventors: Glenn H. Coulter, Lethbridge; Del J. Buckley, Nepean; Bruce S. Scobie, Ottawa, all of Canada

[73] Assignee: Her Majesty the Queen in right of Canada, Canada

[21] Appl. No.: 876,193

[22] Filed: Apr. 30, 1992

[51] Int. Cl.$^5$ .............................................. G01B 5/20
[52] U.S. Cl. .................................... 33/555.4; 33/511
[58] Field of Search ...................... 33/511, 512, 514.1, 33/514.2, 555.1, 555.2, 555.4

[56] References Cited

U.S. PATENT DOCUMENTS

| | | | |
|---|---|---|---|
| 2,129,582 | 9/1938 | Johansson | 33/555.4 |
| 2,609,610 | 9/1952 | Elmes | 33/555.4 |
| 3,514,863 | 6/1970 | Moll | |
| 3,744,140 | 7/1973 | Kyrk | 33/514.1 |
| 3,918,166 | 11/1975 | Mason | |
| 4,569,139 | 2/1986 | Wakeling | 33/555.4 |
| 5,067,246 | 11/1991 | Hesske et al. | 33/555.4 |

FOREIGN PATENT DOCUMENTS 347491 1/1921 Fed. Rep. of Germany.

OTHER PUBLICATIONS

Publication, Theriogenology Mar. 1987 vol. 27 No. 3 Scrotal Circumference of Two-Year-Old Bulls of Several Beef Breeds pp. 1, 4, 5, 10, 12, and 13 of paper presented at 1st International Beef Symposium.
Great Falls, Mont., Jan. 15-17, 1991 by Dr. Glenn H. Coulter on Selection and Management of Beef Bull.

*Primary Examiner*—Thomas B. Will
*Attorney, Agent, or Firm*—Davis, Bujold & Streck

[57] ABSTRACT

An apparatus for performing scrotal circumference measurement on bulls consisting of a casing having an interior cavity, an exterior surface with a concave portion and an opening in the casing providing access to the interior cavity. A gradulated flexible tape is coiled within the interior cavity of the casing. The gradulated flexible tape extends through the opening and has an end secured to the exterior surface of the casing adjacent the concave portiion such that the tape and the concave portion define a circular opening to accommodate a scrotal circumference. The graduations on the tape assign a value to the concave portion thereby providing an accurate circumferential measurement. A spring is positioned within the interior cavity of the casing providing a biasing force of between 1.26 and 2.26 kilograms of tension to draw the tape into the interior cavity of the casing.

4 Claims, 1 Drawing Sheet

APPARATUS FOR PERFORMING SCROTAL CIRCUMFERENCE MEASUREMENT ON BULLS

The present invention relates to an apparatus for performing scrotal circumference measurement on bulls.

BACKGROUND OF THE INVENTION

An important factor in cattle breeding is fertility. Fertility manifests itself in sperm count and semen quality. It is a highly heritable trait. Unless the cattle are selected on the basis of their fertility genetic degeneration of the cattle herd is the inevitable result. Determinations of fertility have focused on bulls, for it is difficult to determine the fertility of cows. It has been established, however, that a bull of above average fertility will have female progeny of above average fertility.

It has been determined that there is a correlation in bulls between testicular weight and sperm production. Sperm production is recognized as being a factor in fertility. There is a correlation between scrotal circumference measurement and weight. As it is not practical to weigh the scrotum of a live bull, efforts to determine fertility have focused upon scrotal measurement. Experts have conducted studies to determine a range of scrotal circumference of bulls according to age and breed. From these ranges they have been able to determine average scrotal circumference and set minimum recommended scrotal circumference in order to avoid genetic degeneration relating to fertility. One such study, a cooperative effort between the Agriculture Canada Research Station at Lethbridge, Alberta and the Western College of Veterinary Medicine at the University of Saskatchewan, is documented in an article by G. H. Coulter, R. J. Mapletoft and W. F. Cates entitled "Scrotal Circumference of Two Year Old Bulls of Several Beef Breeds" which appeared in March 1987 issue Volume 27 No. 3 of Theriogenology.

The measurements and their significance is predicated upon measuring the scrotum with a measuring tape while applying "moderate resistance". It is recognized that care must be taken not to cause trauma to the bull's testes as such trauma results in inflammation which has a detrimental effect on the sperm producing capability of the bull. Depending upon the severity of the trauma such inflammation can effect fertility for weeks or months. On the other hand, if insufficient tension is applied the result gives an inaccurate and misleading indication as to fertility. For example, in the above mentioned article the scrotal circumference for yearling Aberdeen Angus bulls varies between 24.5 and 40.0 centimetres with a mean of 33.9. Bulls with a scrotal circumference below 32 centimetres were not recommended as breeding bulls. An error in measurement of one or more centimetres can have dramatic effects on a breeding program.

Major sales of cattle breeding stock are implementing minimum scrotal measurements as a prerequisite for accepting bulls. It has been discovered, however, that there are only a very few experts in the field who can perform consistent and repeatable manual scrotal circumference measurements. Farmers are relying upon inaccurate scrotal measurements when entering cattle sales. Often they pay entry fees and travel great distances to such sales only to discover that their bulls do not meet the minimum scrotal measurement requirements.

Apparatus exist for performing diverse types of circumferential measurement. The most closely analogous apparatus is U.S. Pat. No. 2,129,582 which issued to Johansson in 1938. This Patent discloses a spring biased tape forming a loop. This type of apparatus is not usable for scrotal measurement without modifications for a number of reasons. On fundamental reason is that the spring tension used in such measuring devices does not approach the "moderate resistance" recommended for scrotal circumference measurement. It is a matter of a great deal of experimentation and study to determine what tension can be equated to "moderate resistance" applied manually by a cattle expert.

SUMMARY OF THE INVENTION

What is required is an apparatus for performing scrotal circumference measurements which will provide consistent and repeatable results without regard to the skill of the user.

According to the present invention there is provided an apparatus for performing scrotal circumference measurement on bulls which is comprised of a casing having an interior cavity, an exterior surface with a concave portion and an opening in the casing providing access to the interior cavity. A graduated flexible tape is coiled within the interior cavity of the casing. The graduated flexible tape extends through the opening and has an end secured to the exterior surface of the casing adjacent the concave portion such that the tape and the concave portion define a circular opening to accommodate a scrotal circumference. The graduations on the tape assign a value to the concave portion thereby providing an accurate circumferential measurement. Biasing means are positioned within the interior cavity of the casing providing a biasing force of between 1.26 and 2.26 kilograms of tension to draw the tape into the interior cavity of the casing.

With the apparatus as described, scrotal measurement can be performed consistently and with repeatability. It is preferred that the biasing force provide 1.76 kilograms of tension as this is generally felt to be optimum for scrotal circumference measurement.

Although beneficial results may be obtained through the use of the apparatus as described, it must be appreciated that there are difficulties inherent in measuring the scrotum of a bull. Bulls are powerful animals, and the scrotum is one of the more sensitive areas of the bull. It is preferred that the measurement be performed with one hand, leaving the other hand free to handle the bull's scrotum to assist in proper placement. Even more beneficial results may, therefore, be obtained when the apparatus has locking means to lock the tape to the casing. This enables a circular opening of a predetermined size to be maintained while the tape is properly positioned around the circumference of the scrotum. The locking means is then released enabling the biasing means to draw the tape tightly around the scrotal circumference.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
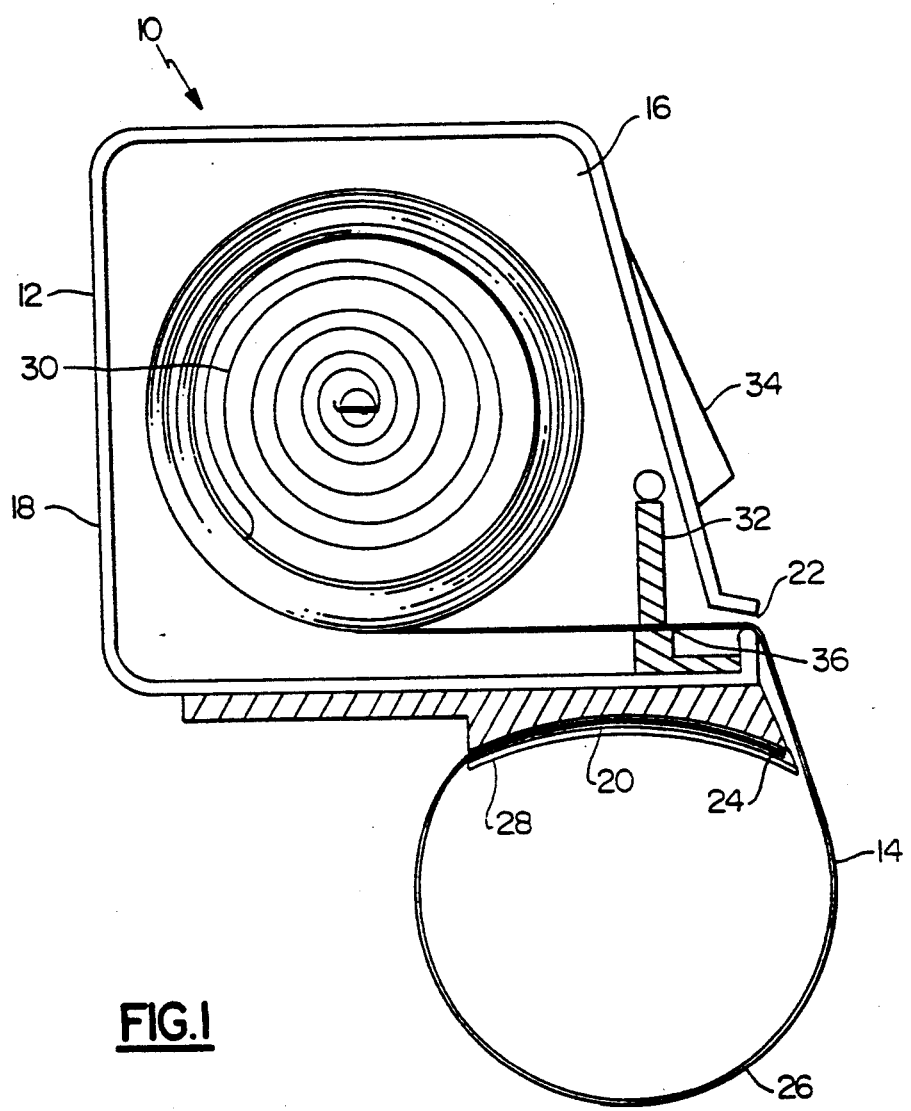
FIG. 1 is a longitudinal section view of an apparatus constructed in accordance with the teachings of the present invention.

The preferred embodiment, an apparatus for performing scrotal circumference measurement on bulls generally identified by reference numeral 10, will now be described with reference to FIG. 1.

The primary components of apparatus 10 consist of a casing 12 and a graduated flexible tape 14. Casing 12 has an interior cavity 16 and an exterior surface 18. Exterior surface 18 has a concave portion 20. An opening 22 extends through casing 12 providing access to interior cavity 16. Tape 14 is coiled within interior cavity 16 of casing 12. Tape 14 extends through opening 22 and has an end 24 secured to exterior surface 18 of casing 12 adjacent concave portion 20. Tape 14 and concave portion 20 define an expandable circular opening, generally identified by reference numeral 26, which is intended to accommodate a scrotal circumference. It must be noted that the graduations (not shown) on tape 14 assign a value to concave portion 20 thereby providing an accurate circumferential measurement. In the illustrated embodiment, this is done by extending tape 14 across concave portion 20 and fixing tape 14 to concave portion 20 by means of a plate 28 secured by rotatable fasteners (not shown). Biasing means are provided in the form of a spring 30 positioned within interior cavity 16 of casing 12. Spring 30 provides a biasing force which draws tape 14 into interior cavity 16 of casing 12. It is important to note that the biasing force provided by spring 30 must be within a range of 1.26 kilograms to 2.26 kilograms of tension. After extensive study 1.76 kilograms of tension is considered the optimum. Locking means are provided in the form of a slidable wedge 32 manually activated by means of switch 34. Slidable wedge 32 locks tape 14 against a shoulder 36 within interior cavity 16 of casing 12.

The use and operation of scrotal measurement apparatus 10 will now be described with reference to FIG. 1. The user draws tape 14 from interior cavity 16 of casing 12 until a circular opening 26 of a size larger that the scrotal circumference being measured is obtained. Tape 14 is then locked in position by means of switch 34 which presses slidable wedge 32 against shoulder 36 to maintain circular opening 26 at its predetermined size. The user then uses one hand to manipulate the scrotum of the bull, and the other hand to slide tape 14 over the scrotum. Once tape 14 is correctly positioned switch 34 is then used to release tape 14. Once tape 14 is released, spring 30 draws tape 14 tightly around the scrotal circumference.

It will be apparent to one skilled in the art that modifications may be made to the illustrated embodiment without departing from the spirit and scope of the invention as defined by the claims.

The embodiments of the invention in which an exclusive property or privilege is claimed are defined as follows:

1. An apparatus for performing scrotal circumference measurement on bulls, comprising:
    a. a casing having an interior cavity, an exterior surface with a concave portion and an opening in the casing providing access to the interior cavity;
    b. a graduated flexible tape coiled within the interior cavity of the casing, the graduated flexible tape extending through the opening and having an end secured to the exterior surface of the casing adjacent the concave portion such that the tape and the concave portion define a circular opening to accommodate a scrotal circumference, and the graduations on the tape assign a value to the concave portion thereby providing an accurate circumferential measurement; and
    c. biasing means positioned within the interior cavity of the casing providing a biasing force of between 1.26 and 2.26 kilograms of tension to draw the tape into the interior cavity of the casing.

2. The apparatus for performing scrotal circumference measurement on bulls as defined in claim 1, the biasing means providing a biasing force of 1.76 kilograms of tension.

3. The apparatus for performing scrotal circumference measurement on bulls as defined in claim 1, having locking means to lock the tape to the casing whereby a circular opening of a predetermined size is maintained until the locking means is released whereupon the biasing means draws the tape tightly around the scrotal circumference.

4. An apparatus for performing scrotal circumference measurement on bulls, comprising:
    a. a casing having an interior cavity, an exterior surface with a concave portion and an opening in the casing providing access to the interior cavity;
    b. a graduated flexible tape coiled within the interior cavity of the casing, the graduated flexible tape extending through the opening and having an end secured to the exterior surface of the casing adjacent the concave portion such that the tape and the concave portion define a circular opening to accommodate a scrotal circumference, and the graduations on the tape assign a value to the concave portion thereby providing an accurate circumferential measurement;
    c. biasing means in the form of a spring positioned within the interior cavity of the casing providing a biasing force of 1.76 kilograms of tension to draw the tape into the interior cavity of the casing; and
    d. locking means in the form of a manually activated slidable wedge to lock the tape against a shoulder within the interior cavity of the casing whereby a circular opening of a predetermined size is maintained until the locking means is released whereupon the biasing means draws the tape tightly around the scrotal circumference.

* * * * *